United States Patent [19]

Vogel et al.

[11] 4,070,179

[45] Jan. 24, 1978

[54] PLANT GROWTH REGULATION WITH N-(2-ALKOXY-ETHYL)-N-CHLOROACETYL-2,3,6-TRIMETHYL-ANILINES

[75] Inventors: Christian Vogel, Binningen; Rudolf Aebi, Basel, both of Switzerland

[73] Assignee: Ciba-Geigy Corporation, Ardsley, N.Y.

[21] Appl. No.: 730,392

[22] Filed: Oct. 7, 1976

Related U.S. Application Data

[63] Continuation-in-part of Ser. No. 602,341, Aug. 6, 1975, abandoned, which is a continuation of Ser. No. 438,519, Jan. 13, 1974, abandoned.

[30] Foreign Application Priority Data

Feb. 7, 1973  Switzerland .......................... 1757/73

[51] Int. Cl.$^2$ .......................................... C07C 103/375
[52] U.S. Cl. .................................... 71/118; 260/562 B
[58] Field of Search ...................... 260/562 B; 71/118

[56] References Cited

U.S. PATENT DOCUMENTS

| | | | |
|---|---|---|---|
| 2,863,752 | 12/1958 | Hamm et al. ........................ | 260/562 |
| 3,268,324 | 8/1966 | Hamm et al. ........................ | 260/562 |
| 3,442,945 | 5/1969 | Olin ..................................... | 260/562 |
| 3,547,620 | 12/1970 | Olin ..................................... | 260/562 |

FOREIGN PATENT DOCUMENTS

| | | | |
|---|---|---|---|
| 1,337,529 | 8/1963 | France ................................ | 260/562 |
| 1,419,116 | 10/1965 | France ................................ | 260/562 |
| 1,903,198 | 8/1970 | Germany ............................. | 260/562 |
| 1,008,851 | 11/1965 | United Kingdom ................. | 260/562 |
| 1,283,163 | 7/1972 | United Kingdom ................. | 260/562 |

*Primary Examiner*—Arthur P. Demers
*Attorney, Agent, or Firm*—Harry Falber

[57] ABSTRACT

N-(2'-alkoxy-ethyl)-N-chloroacetyl-2,3,6-trimethyl-anilines wherein the alkoxy residue is methoxy, ethoxy or isopropoxy are effective weedkillers in plant crops, such as soya and cotton. They may also be used for retarding plant growth.

4 Claims, No Drawings

PLANT GROWTH REGULATION WITH N-(2-ALKOXY-ETHYL)-N-CHLOROACETYL-2,3,6-TRIMETHYL-ANILINES

CROSS REFERENCE

This application is a continuation-in-part of abandoned application Ser. No. 602,341, filed Aug. 6, 1975, which in turn is a continuation of abandoned application Ser. No. 438,519, filed Jan. 13, 1974.

The present invention provides three new N-substituted haloacetanilides as well as plant growth regulating agents which contain them as active substances and furthermore a method of selectively controlling weeds in crops of cultivated plants, such as cotton and soybeans, which comprises the use of the active substances or of agents which contain them.

Reference is made to the following patent specifications as representing the prior art in respect of plant regulating haloacetanilides: French Pat. Nos. 1,337,529, 1,419,116 and 2,028,991, Belgian Pat. No. 746,288, and U.S. Pat. Nos. 2,863,752, 3,442,945 and 3,547,620.

It is the task of this invention to provide haloacetanilides with improved plant regulating properties, i.e. which in low rates of application control a larger number of weed species, and, above all, highly resistant weeds, distinctly better than the known haloacetanilides without having any adverse effect on cotton and soya cultures.

Compared with the compounds known up till now, the new N-substituted haloacetanilides according to the invention differ fundamentally in their improved long lasting activity on grasses and dicotyledonous weeds and their tolerance by soybeans and cotton.

The new compounds correspond to the generic formula

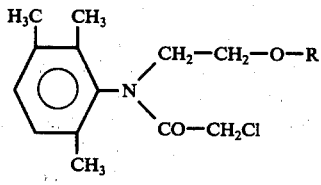

wherein R represents methyl, ethyl or isopropyl, and may accordingly be called
No. 1 N-(2'-methoxy-ethyl)-N-chloroacetyl-2,3,6-trimethylaniline or 2,3,6-trimethyl-N-2'-methoxyethyl -N-chloroacetanilide,
No. 2 N-(2'-ethoxy-ethyl)-N-chloroacetyl-2,3,6-trimethylaniline or 2,3,6-trimethyl-N-2'-ethoxyethyl-N-chloroacetanilide,
No. 3 N-(2'-isopropoxy-ethyl)-N-chloroacetyl-2,3,6-trimethylaniline or 2,3,6-trimethyl-N-2'-isopropoxyethyl-N-chloracetanilide.

They may be manufactured by reacting an N-substituted aniline of the formula II

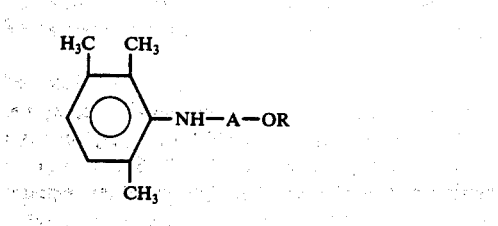

with a chloroacetylating agent, preferably an anhydride or halide of chloroacetic acid. In formula II the symbol R has the same meaning as given under formula I.

It is also possible to manufacture the compounds of the formula I in such a way that 2,3,6-trimethyl-aniline is reacted with
2-haloethanol or ethylene oxide to introduce the hydroxyalkyl chain $-CH_2-CH_2-OH$;
then the resulting compound of the formula IIa

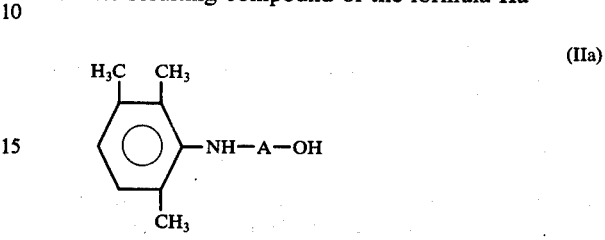

is chloroacetylated preferably with an anhydride or halide of chloroacetic acid, and, finally, the still free OH group is etherified in acid medium (e.g. HCl, $H_2SO_4$) under mild conditions and in conventional manner with methanol, ethanol or isopropanol.

The reactions can be carried out in the presence or absence of solvents or diluents which are inert towards the reactants. Examples of suitable solvents or diluents are: aliphatic, aromatic or halogenated hydrocarbons, such as benzene, toluene, xylene, petroleum ether, chlorobenzene, methylene chloride, ethylene chloride, chloroform; ethers and ethereal compounds, such as dialkyl ethers, dioxan, tetrahydrofuran; nitriles, such as acetonitrile; N,N-dialkylated amides, such as dimethyl formamide; also dimethyl sulphoxide, and also mixtures of these solvents.

As suitable chloroacetylating agents there are preferably used chloroacetic anhydride, and chloroacetic halides, such as chloroacetyl chloride. However, it is also possible to carry out the reaction with chloroacetic acid, its esters or amides. The reaction temperatures are between 0° and 200° C, preferably between 20° and 100° C. Often, especially if chloroacetyl halides are used, the chloroacetylation is carried out in the presence of an acid acceptor. Suitable acid acceptors are: tertiary amines, such as trialkylamines, e.g. triethylamine, pyridine and pyridine bases, or in organic bases, such as the oxides and hydroxides, hydrogen carbonates and carbonates or alkali and alkaline earth metals. Furthermore, it is also possible to use the corresponding aniline of the formula II as acid acceptor, in which case a surplus must be used.

Starting materials similar to those of the formula II and corresponding hydroxyalkyl derivatives (R=H) are known, e.g. from U.S. Pat. Nos. 2,381,071, 2,759,943 as well as from Am.Soc. 84, 743, and Bull. Soc. Chim. France 1962, 303 and 1965, 2037. These starting materials, as well as those not yet described in the literature can be manufactured easily by one of the following known methods, for example:

a. by condensation of 2,3,6-trimethyl-aniline with a carbonyl compound of the formula III

in which R represents methyl, ethyl or isopropyl and simultaneous or subsequent catalytic hydrogenation of the resulting azomethine of the formula IV

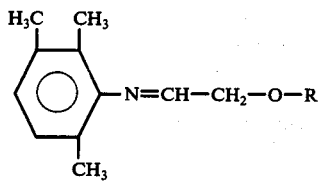

to yield compounds of the formula I, b. by reaction of 2,3,6-trimethyl-aniline with a compound of the formula V

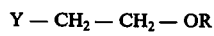

Y — CH$_2$ — CH$_2$ — OR        (V)

wherein R is methyl, ethyl or isopropyl and Y represents a halogen atom or another acid radical, in particular an arylsulphonic acid radical. Compounds of the formula V with benzenesulphonic acid radicals Y are described e.g. in Can. J. Chem. 33, 1207, and those with tosyloxy radicals (CH$_3$—C$_6$H$_4$—SO$_3$—) in British patent specification No. 869,083.

There are, of course, a number of other processes for the manufacture of the starting materials of the formula II from trimethyl aniline.

The following Examples illustrate the process according to the invention, including the manufacture of starting materials.

EXAMPLE 1 a. Preparation of the intermediate

A solution comprising 595 g (4.4 moles) of 2,3,6-trimethylaniline in 1 liter of toluene is heated to boiling 503 g (2.2 moles) of p-toluenesulfonic-acid-(2-methoxyethyl)-ester is dropped thereto within 6 hrs. The reaction mixture is cooled, poured into 2 liter of isopropylethylether and the solid residue filtered off and washed with diethylether. The combined filtrates are evaporated. After distillation in vacuo 301 g (i.e. 71% theoretical amount) of N-(2-methoxyethyl)-2,3,6-trimethylaniline are obtained, b-p. 141°-144° C/14 Torr.

b. 23.3 g(0.22 moles) of sodium carbonate and 36.5 g (0.19 moles) of the intermediate obtained under a) are suspended in benzene. 17.5 ml (0.22 moles) of chloroacetylchloride are dropped thereto withins 45 minutes and the temperature increasing to 50° C. Upon completion of the reaction (2 hours later), the reaction mixture is diluted with 400 ml of water and 200 ml of diethyl ether. The organic layer is separated off, dried over sodium sulfate, filtered and evaporated. After distillation of the oily residue 47.5 g (92% of theoretical amount) of 2,3,6-trimethyl-N-2'-methoxyethyl-chloroacetanilide are obtained, b.p. 118°-120° C/0.01 Torr. (compound No. 1).

EXAMPLE 2 a. Preparation of the intermediate

According to the method of Example 1a 553 g (2.26 moles) of p-toluenesulfonic-acid-(2-ethoxyethyl)-ester are added to a solution of 607 g (4.5 moles) 2,3,6-trimethylaniline in 1 liter of toluene. 317 g(68% of theoretical amount) of N-(2-ethoxyethyl)-2,3,6-trimethyl-aniline are obtained, b.p. 150°-152° C / 14 Torr.

b. The acylation step is carried out according to Example 1b. The desired product, 2,3,6-trimethyl-N-2'-ethoxyethylchloroacetanilide is obtained as yellow oil, b.p. 121°-123° C/0.01 Torr.

EXAMPLE 3 a. Preparation of the intermediate

A solution of 81 g (0.6 moles) of 2,3,6-trimethylamine and 77.3 g (0.3 moles) of p-toluenesulfonic-acid-(2-isopropoxyethyl)-ester in 100 ml of toluene are heated under reflux for 18 hour. The still hot reaction mixture is poured into 500 ml of isopropylether. After cooling the precipitate is filtered under suction and the filtrate is evaporated and fractionally distilled. 46.0 g (69% of theoret. amount) of N-(2-isopropoxyethyl)-2,3,6-trimethylaniline are obtained, b.p. 80°-84° C/0.001 Torr.

b. The acylation of the intermediate obtained is carried out according to the method of Example 1b:

46.0g (0.208 moles) of intermediate in
200 ml of benzene,
25.5 g (0.24 moles) of sodium carbonate, and
19.1 ml (0.24 moles) of chloroacetylchloride give 55.4 g (89.5% of theoretical amount) of 2.3.6-N-2'-isopropoxyethyl-chloroacetanilide (yellow oil, b.p. 124°-126° C/0.001 Torr.

The three active substances according to the invention are stable compounds and possess very good herbicidal properties against annual grasses and related plants of the genera Setaria sp., Digitaria, etc. against grasses such as Lolium species, *Avena fatua* (wild oats), Alopecurus myos., Eleusine, *Eriochloa gracilis*, and against dicotyledonous weeds such as Amaranthus, Sesbania, Chrysanthemum, *Sida spinosa*, Galium, Pastinaca, without causing damage to the cultivated plants in respect of which the use of the active substances is intended, for example alfalfa, ground nuts, sugar beet, Brassica species such as rape, but also cereals, such as rice, preferably leguminous plants, such as soybeans, beans, peas and lentils, as well as cotton.

The active substances are applied before, at or after the germination of the cultivated plants and of the weeds and grasses; preemergence or at emergence application is preferred. The rates of application are between 0.1 and 10 kg of active substance per hectare. But in preemergent application the weeds are virtually destroyed using a rate of application as low as 0.25 kg of active substances per hectare. Normally up to 10 kg of active substance per hectare are used to prevent railway embankments, factory grounds, roads etc. from becoming overgrown with weeds.

Furthermore, the active substances of the formula I, when applied postemergent, also exhibit growth retarding properties in that they delay the growth in height and increase the tillering of grasses (e.g. in existing grass plantations such as lawns, embankments along main roads, railways or bodies of water). Profusely and rapidly seeding weeds are inhibited in their germination and emergence and so removed from cultivations of crop plants.

As already mentioned, herbicidal haloacetanilides of comparable constitution are known from the literature. However, these either have only alkoxymethyl groups at the nitrogen atom (U.S. Pat. No. 3,547,620) or in one ortho-position of the phenyl radical carry other tertiary alkyl substituents such as in particular tert. butyl (French Pat. No. 1,337,529).

It is disclosed in the literature that the N-alkoxymethyl derivatives represent the best products and are superior at all events to the corresponding N-alkoxyethyl and N-alkoxypropyl derivatives (U.S. Pat. No. 3,547,620, Example 85). On the basis of this publication, one skilled in the art had to assume that N-substituted haloacetanilides with alkoxy groups which are bonded to the nitrogen atom of the anilide through alkylene radicals with 2 chain members, regardless of how they are substituted in the phenyl nucleus, are not suitable as herbicides for practical purpose.

The surprising discovery has now been made that the 2,3,6-trimethylaniline derivatives of the formula I according to the invention, which do not have the supposedly most favourable constitution for the herbicidal activity as claimed in U.S. Pat. No. 3,547,620, are superior to these N-alkoxymethyl-2,(6)-(di)-alkyl-chloroacetanilides and other closely related compounds described in the literature in the long lasting selective control of weeds.

EXAMPLE 4

Control of wild millet species, other grasses and monocotyledonous weeds in various cultures of crop plants (preemergence method)

One day after the test plants have been sown in seed dishes, dilute aqueous suspensions of the active substances are sprayed in such concentrations on the surface of the soil as to correspond to rates of application of 4 kg and 2 kg per hectare. The seed dishes are kept at 22° and 25° C and about 70% relative humidity. The test is evaluated after 28 days according to the following linear rating:

9 = plants undamaged (as control test)
1 = plants destroyed
8-2 = intermediate stages of damage
— = not tested Known haloacetanilides were used as comparison compounds:
Compound A: 2-methyl-N-(1'-methoxyprop-2'-yl)-N-chloroacetanilide (French Pat. No. 2,028,991)
Compound B: 2,6-diethyl-N-(methoxymethyl)-chloroacetanilide (commercial product) (U.S. Pat. No. 3,547,620).

important weeds such as Rottboellia, Avena fatua, Sesbania exaltata, Chrysanthemum and Pastinaca.

EXAMPLE 5

Growth inhibition in grasses (postemergence method)

Seeds of the grasses *Lolium perenne*, *Poa pratensis*, *Festuca ovina*, and *Dactylis glomerata* were sown in plastic dishes filled with an earth/turf/sand mixture. After 3 weeks the germinated grasses were cut back to a height of 4 cm above the soil and 2 days later sprayed with aqueous spray broths of active substances of the formula 1. The amount of active substance corresponded to a rate of application of 5 kg of active substance per hectare. Fourteen days after application the growth of the grasses was evaluated according to the following linear rating:

1 = strong inhibition (no growth from the time of application)
9 = no inhibition (growth as untreated control)

Very strong growth inhibition was achieved with compounds 1, 2 and 3 according to the invention (rating 1 to 3).

The agents according to the invention are manufactured in known manner by intimately mixing and/or grinding active substances of the formula I with the suitable carriers, optionally with the addition of dispersants or solvents which are inert towards the active substances. The active substances may take and be used in the following forms:

Solid forms:

Dusts, tracking agents, granules, coated granules, impregnated granules and homogenous granules, Liquid forms:

a. active substances which are dispersible in water: wettable powders, pastes, emulsions;
b. solutions.

To manufacture solid forms (dusts, tracking agents), the active substance are mixed with solid carriers. Suitable carriers are, for example: kaolin, talcum, bolus, loess, chalk, limestone, ground limestone, attaclay, do- Table 1

| Comp. No. | Rate of application in kg AS/ha | Echinochloa | Setaria | Digitaria | Rottboellia | Cyperus | Alopecurus | Lolium | Avena fatua | Sesbania exalt. | Amaranthus | Chrysanthemum | Pastinaca | cotton | soya |
|---|---|---|---|---|---|---|---|---|---|---|---|---|---|---|---|
| 1 | 4 | 1 | 1 | 1 | 1 | 1 | 1 | 1 | 2 | 1 | 1 | 2 | 1 | 8 | 8 |
|  | 2 | 1 | 1 | 1 | 1 | 1 | 1 | 2 | 2 | 2 | 1 | 2 | 2 | 9 | 8 |
| 2 | 4 | 1 | 1 | 1 | 1 | 1 | 1 | 1 | 2 | 1 | 1 | 2 | 1 | 9 | 8 |
|  | 2 | 1 | 1 | 1 | 2 | 1 | 1 | 2 | 2 | 2 | 1 | 2 | 1 | 9 | 8 |
| 3 | 4 | 1 | 1 | 1 | 2 | 1 | 2 | 1 | 2 | 2 | 1 | 2 | 1 | 9 | 9 |
|  | 2 | 1 | 1 | 1 | 2 | 1 | 2 | 2 | 2 | 2 | 1 | 3 | — | 9 | 8 |
| A | 4 | 1 | 1 | 1 | 4 | 1 | 1 | 1 | 3 | 6 | 1 | 5 | 6 | 8 | 8 |
|  | 2 | 1 | 1 | 1 | 7 | 1 | 2 | 3 | 4 | 8 | 3 | 6 | 7 | 8 | 8 |
| B | 4 | 1 | 1 | 1 | 4 | 1 | 1 | 1 | 2 | 9 | 1 | 4 | 2 | 7 | 8 |
|  | 2 | 1 | 1 | 1 | 4 | 2 | 2 | 2 | 2 | 9 | 1 | 6 | 4 | 9 | 8 |

It is evident from the comparison results that the selectivity of the compounds of the present invention in the control of weeds and protection of crop plants is distinctly better than that of the closest comparable known compounds. At the rate of application of 2 kg of active substance per hectare the comparative compounds A and B do not exhibit satisfactory control of lomite, diatomacous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, urea, ground vegetable products, such as corn meal, bark dust, sawdust, nutshell meal, cellulose powder, residues of plant extractions, activated charcoal etc. These substances can either be used singly or in admixture with one another.

The particle size of the carriers for dusts is advantageously up to 0.1 mm, for tracking agents from about 0.075 to 0.2 mm, and for granules 0.2 mm or larger.

The solid forms contain the active substances in concentrations from 0.1 % to 80%.

To these mixtures can also be added additives which stabilize the active substance and/or non-ionic, anionic and cationic surface active substances, which for example improve the adhesion of the active ingredients on plants or parts of plants (adhesive and agglutinants) and/or ensure a better wettability (wetting agents) and dispersibility (dispersing agents). Examples of suitable adhesives are the following: olein/chalk mixture, cellulose derivatives (methyl cellulose, carboxymethy cellulose), hydroxyethyl glycol ethers of monoalkyl and dialkyl phenols having 5 to 15 ethylene oxide radicals per molecule and 8 to 9 carbonatoms in the alkyl radical, lignin sulphonic acids, their alkali metal and alkaline earth metal salts, polyethylene glycol ethers (carbowaxes), fatty alcohol polyethylene glycol ether having 5 to 20 ethylene oxide radicals per molecule and 8 to 18 carbon atoms in the fatty alcohol moiety, condensation product of urea and formaldehyde, and also latex products.

The water-dispersible concentrates of the active substance i.e. wettable powders, pastes and emulsifiable concentrates, are agents which can be diluted with water to any concentration desired. They consist of active substance, carrier, optionally additives which stabilize the active substance, surface-active substances and anti-foam agents and, optionally, solvents. The active substance concentrations in these agents are from 5–80%.

Wettable powders and pastes are obtained by mixing and grinding the active substances with dispersing agents and pulverulent carriers in suitable apparatus until homogeneity is attained. Carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde, condenation products of naphthalene or naphthalene sulphonic acids with phenol and formaldehyde, as well as alkali, ammonium and alkaline earth metal salts of lignin sulphonic acid, in addition, alkylaryl sulphonates, alkali and alkaline earth metal salts of dibutyl naphthalene sulphonic acid, fatty alcohol sulphates such as salts of sulphated hexadecanols, heptadecanols, octadecanols, and salt of sulphated fatty alcohol glycol ethers, the sodium salt of oleoyl ethionate, the sodium salt of oleoly methyl tauride, ditertiary acetalene glycols, dialkyl dilauryl ammonium chloride and fatty acid alkali and alkaline earth salts.

Suitable anti-foam agents are silicones. The active substances are so mixed, ground sieved and strained with the additives mentioned above that, in wettable powders, the solid particle size of from 0.02 to 0.04 and in pastes, of 0.03 is not exceeded. To produce emulsifiable concentrates and pastes, dispersing agents such as those given in the previous paragraphs, organic solvents and water are used. Examples of suitable solvents are: alcohols, benzene, xylenes, toluene, dimethyl sulphoxide, N,N-dialkylated amides, N-oxides of amines, especially trialkylamines, and mineral oil fractions boiling between 120° and 350° C. The solvents must be practically odourless, not phytotoxic, inert to the active substances and may not have too low a flash point.

Furthermore, the agents according to the invention can be applied in the form of solution. For this purpose the active substance, or several active substances of general formula I, is dissolved in suitable organic solvents, mixtures of solvents or in water. Aliphatic and aromatic hydrocarbons, chlorinated derivatives thereof, alkyl naphthalenes and mineral oils singly or in admixture, can be used as organic solvents. The solutions contain the active substance in a concentration range from 1% to 20%. These solutions can either be applied with the acid of a propellant gas (spray) or with special spray (as aerosol).

The agents described according to the invention can be mixed with other biocidally active substances or agents. Thus in order to broaden the activity spectrum the new agents may contain, for example, insecticides, fungicides, bactericides, fungistatics, bacteriostatics, nematocides or further herbicides, in addition to the cited active substances of the formula I. The agents according to the invention may also contain plant fertilisers, trace elements etc.

The active substances of the formula I can, for example, be formulated as follows. The parts denote parts by weight.

Granules

The following substances are used to manufacture 5% granules:

5 parts of active substance of the formula I
0.25 part of epichlorohydrin,
0.25 part of cetyl polyglycol ether,
3.50 parts of polyethylene glycol ether,
91 parts of kaolin (particle size: 0.3–0.8 mm).

The active substance is mixed with epichlorohydrin and the mixture dissolved in 6 parts of acetone, then polyethylene glycol ether and cetyl polyglycol ether are added. The resulting solution is sprayed on kaolin and then evaporated in vacuo.

Wettable powder

The following constituents are used to manufacture (a) a 50%, (b) a 25% and (c) a 10% wettable powder:

(a)

50 parts of active substance of the formula I,
5 parts of sodium dibutylnaphthalene sulphonate,
3 parts of naphthalenesulphonic acid/phenolsulphonic acid/formaldehyde condensate (3:2:1),
20 parts of kaolin,
22 parts of champagne chalk;

(b)

25 parts of active substance of the formula I,
5 parts of oleylmethyltaurid-sodium salt,
2.5 parts of naphthalenesulphonic acid/formaldehyde condensate,
0.5 part of carboxymethyl cellulose,
5 parts of neutral potassium-aluminium-silicate,
62 parts of kaolin;

(c)

10 parts of N-(2'-methoxyethyl)-2,3,6-trimethyl-chloro acetanilide, 3 parts of a mixture of the sodium salts of saturated fatty alcohol sulphates,
5 parts of naphthalenesulphonic acid/formaldehyde condensate,
82 parts of kaolin.

The indicated active substance is applied to the corresponding carriers (kaolin and chalk) and then these are mixed and ground, to yield wettable powders of excellent wettability and having an excellent capacity for forming suspension. By diluting these wettable powders with water it is possible to obtain suspensions of any desired concentration.

Paste

The following substances are used to manufacture a 45% paste:

45 parts of active substance of the formula I,
5 parts of sodium aluminium silicate,
14 parts of cetyl polyglycol ether with 8 mols of ethylene oxide,
1 part of oleyl polyglycol ether with 5 mols of ethylene oxide,
2 parts of spindle oil,
10 parts of polyethylene glycol,
38-18 parts of water.

The active substance is intimately mixed with the additives in appropriate devices and ground. A paste is obtained from which, by dilution with water, is possible to manufacture suspensions of every desired concentration of active substance.

Emulsion Concentrate

To manufacture a 25% emulsion concentrate
25 parts of active substance of the formula I,
b 5 parts of a mixture of nonylphenolpolyoxy-ethoxyethylene and calcium dodecylenesulphonate,
35 parts of 3,5,5-trimethyl-2-cyclohexan-1-one,
40-30 parts of dimethyl formamide, are mixed together this concentrate can be diluted with water to give emulsions in desired concentrations. Such emulsions are suitable for controlling weeds in cultures of crop plants.

What we claim is:
1. A compound of the formula I

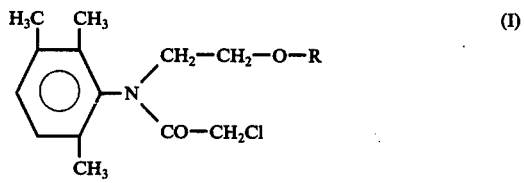

wherein R represents methyl, ethyl or isopropyl.
2. A composition for controlling plant growth which comprises as active ingredient an effective amount of a compound according to claim 1 plus an inert carrier.
3. A method of selectively controlling weeds in culture of crop plants, which comprises applying to the locus thereof an effective amount of a compound according to claim 1.
4. A method according to claim 3 wherein the crop plants are soya and cotton.

* * * * *